US00PP10475P

United States Patent [19]

Koppe

[11] Patent Number: Plant 10,475

[45] Date of Patent: Jun. 30, 1998

[54] BEGONIA PLANT NAMED 'BETULIA'

[75] Inventor: Lubbertus H. Koppe, Ermelo, Netherlands

[73] Assignee: M. Koppe B.V., Am Ermelo, Netherlands

[21] Appl. No.: 673,826

[22] Filed: Jun. 27, 1996

[51] Int. Cl.[6] ..... A01H 5/00

[52] U.S. Cl. ..... Plt./87.18

[58] Field of Search ..... Plt./87.18

[56] References Cited

U.S. PATENT DOCUMENTS

P.P. 9,523 4/1996 Koppe ..... Plt./87.18

OTHER PUBLICATIONS

Upov Rom, DISK Jan. 1997 Name Search Printout, 1997.

*Primary Examiner*—Howard J. Locker
*Assistant Examiner*—Kent L. Bell
*Attorney, Agent, or Firm*—Foley & Lardner

[57] ABSTRACT

A Begonia plant named 'Betulia' particularly characterized by continuous flowering throughout the year, semi-double to double-type flowers with many red colored flowers, excellent branching habit, compact and round growth habit, dark foliage and outstanding deeping quality through the winter.

5 Drawing Sheets

The present invention relates to a new and distinctive cultivar of begonia plant, botanically known as *Begonia hiemalis* Fotch and known by the cultivar name 'Betulia'.

The new cultivar is a random mutation out of the begonia variety 'Barkos', disclosed in a patented application of the inventor (PP 9,523), and was discovered by Lubbertus H. Koppe in July 1991 in Ermelo, The Netherlands.

The new cultivar was asexually propagated by the inventor for the first time in July 1992 in Ermelo, The Netherlands. Asexual reproduction of 'Betulia' by means of leaf cuttings has demonstrated that the unique features of the new cultivar are stable through successive propagations.

The following characteristics distinguish the new begonia from its parent and other begonias commercially known and used in the floriculture industry:

1. 'Betulia' flowers throughout the year whereas many other begonias flower only under conditions of long day-length.
2. 'Betulia' has an excellent branching habit and there is no need for pinching.
3. 'Betulia' produces more flowers than 'Barkos'.
4. The flowers of 'Betulia' are much smaller than those of 'Barkos'.
5. The flowers of 'Betulia' are semi-double to double in contrast to those of 'Barkos' which are strongly double flowering.
6. 'Betulia' produces more leaves that are smaller in size than those produced by 'Barkos'.
7. The plants of 'Betulia' are smaller than those of 'Barkos'.
8. The growth habit of 'Betulia' is more compact and rounder than 'Barkos'.
9. 'Betulia' exhibits excellent outdoor keeping quality.

Of the many commerical cultivars known to the present inventors, the most similar in comparison to 'Betulia' is 'Bellona', which is described in copending application Ser. No. 08/673,827 filed Jun. 27, 1996 Chart A compares certain characteristics of 'Betulia' to those same characteristics of 'Bellona'.

CHART A

| Characteristic | 'Betulia' | 'Bellona' |
|---|---|---|
| Flower type | Semi-double to double | Double |
| Flower number | 12–15 from one stem out of axillary bud | 7–9 from one stem out of axillary bud |
| Plant size | 25–28 cm (height) × 30–34 cm (width) | 28–32 cm (height) × 33–36 cm (width) |
| Petal number | About 10 per flower | About 20 per flower |
| Foliage size | Smaller than 'Bellona' | Larger than 'Betulia' |

In general comparison to 'Bellona' , 'Betulia' is smaller and produces flowers that are semi-double to double-type, smaller, and fewer in number.

The accompanying color photographs of 'Betulia' were taken on Oct. 8, 1995 in 's-Gravenzande, The Netherlands. Photographs were made of 4 month old plants in 17 cm pots.

Sheet 1 is a top perspective and

Sheet 2 is top-side perspective of 'Betulia'.

Sheet 3 shows the upper side of a mature leaf from the new variety.

Sheet 4 shows the inflorescence and

Sheet 5 is a close-up of a flower from 'Betulia'.

The new cultivar 'Betulia' is principally distinguishable from other begonia varieties by its distinctive branching habit. The numerous branches produced by the new variety reduces the need to pinch the plant to produce new shoots. 'Betulia' also exhibits excellent outdoor keeping quality.

Asexual reproduction has demonstrated that the combination of characteristics herein disclosed for the new cultivar are firmly fixed and stable through successive generations. 'Betulia' has not been observed under all possible environmental conditions. The phenotype may vary with variations in environment such as temperature, light intensity and day length without a change in genotype.

The following is a detailed description of the new begonia cultivar based on plants produced under commercial practices in Maasland, The Netherlands. Color references are made to The Royal Horticulture Society (R.H.S.) Colour Chart except where general terms of ordinary dictionary significance are used.

Parentage: Mutation of *Begonia hiemalis* cv. 'Barkos'.

*Classifications.*—*Begonia hiemalis* Foch cv. 'Betulia'.

Propagation:

*Type cutting.*—Top and/or leaf cutting.

*Time to root.*—5 weeks at 20–22° C. in winter and summer.

*Rooting habit.*—Spreading and the roots do not form tubers.

*Time for shoot development.*—5–7 weeks by leaf cutting.

Growing conditions:

*Temperatures.*—For the first 4–5 weeks day and night 20°C then 19° C. until flowering.

*Photoperiodic treatments.*—4 weeks after potting use 2 weeks short days followed by long day conditions.

*Growth retardation.*—Cycocel.

Plant description: The following description is based on observations taken of 4 month old plants grown in 17 cm pots.

*Form.*—Spreading.

*Height.*—25–28 cm.

*Width.*—30–34 cm.

*Branching.*—Very good.

*Growth habit.*—Compact and round.

Foliage: Dark green.

*color.*—Upper side: R.H.S. 147A. Under side: R.H.S. 148B.

*Veination.*—Palmate, color R.H.S. 148D.

*Shape.*—More or less reniform.

*Size.*—Juvenile leaf: Width 60 mm, length 40 mm. Mature leaf: Width 85 mm, length 75 mm.

*Margin.*—Bi-serrate.

*Tip.*—Attenuated.

*Base.*—Narrow sinus between basal lobes.

*Attachment.*—Stalked, length of petiole 60mm.

*Texture.*—A little stif and leathery.

Flowering Description:

*Flowering habit.*—floriferous with branched inflorescence.

*Natural flowering season.*—Mid-February through November.

*Flower buds.*—Sepals are light green turning a little reddish at the tip.

*Flowers borne.*—From axillary buds.

Flower: Semi-double to double-flowering.

*Pistil.*—Absent.

*Sramen.*—Absent.

*Quantity.*—12–15 flowers from one stem out of axillary bud.

Petals:

*Color.*—Outer petal, upper side: R.H.S. 45B. Outer petal, under side: R.H.S. 45C. Inner petal, upper side: R.H.S. 45B. Inner petal, under side: R.H.S. 45C.

*Number.*—About 10 per flower.

*Margin.*—Entire to slightly crenate toward the tip.

*Shape.*—Very broad obovate.

*Length.*—Outer petal: 20–24 mm. Inner petal: ca. 20 mm.

*Width.*—Outer petal: 24–≈mm. Inner petal: ca. 22 mm.

Flower longevity: Very good.

Disease resistance: No resistance but good tolerance against mildew.

General Observations:

The begonia cultivar 'Betulia' grows vigorously and produces excellent cuttings that root well. 'Betulia' produces numerous branches without pinching, and a large quantity of leaves. The new variety is very floriferous and exhibits excellent keeping quality.'Betulia' typically holds its blooms about 8–12 weeks in summer and about 6–9weeks in winter. The cultivar also keeps its flowers and does not fade when planted outdoors. 'Betulia' produces semi-double to double type flowers that maintain their red color.

I claim:

1. A new and distinct begonia plant named 'Betulia', as described and illustrated.

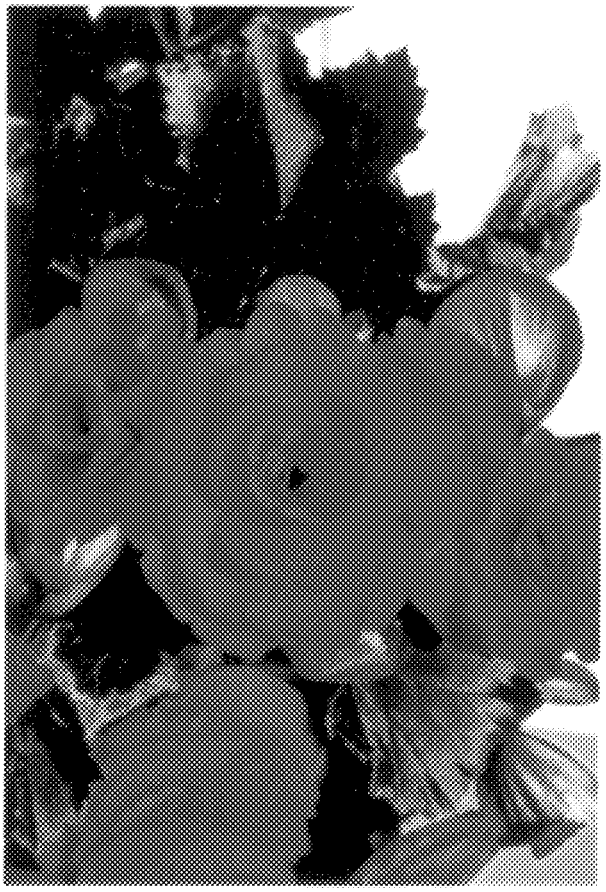

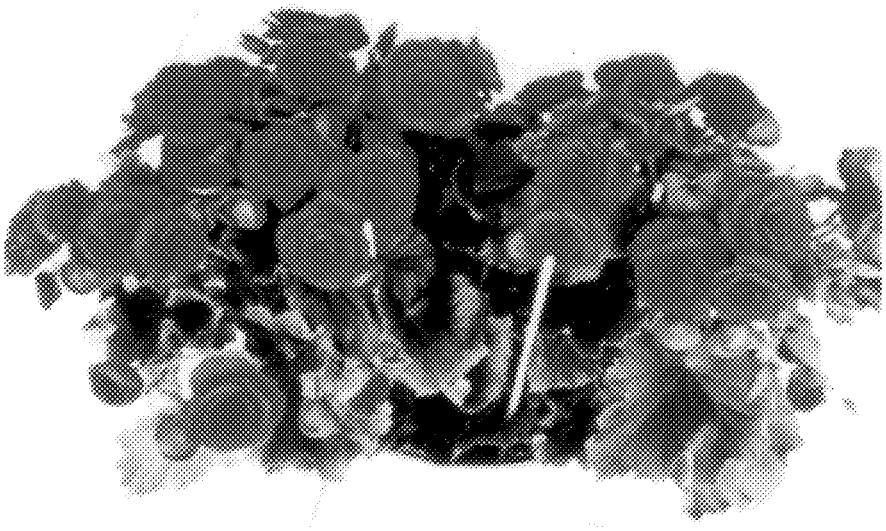

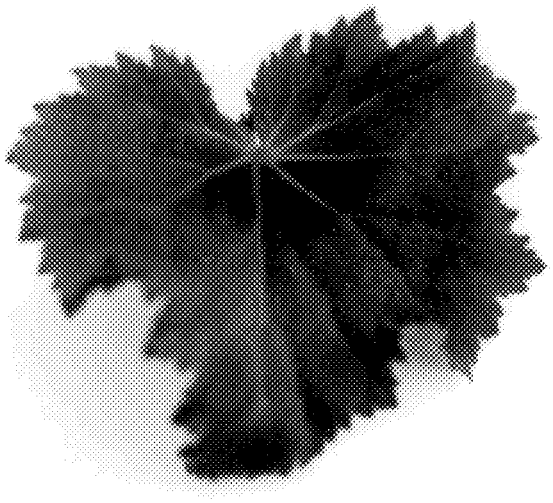

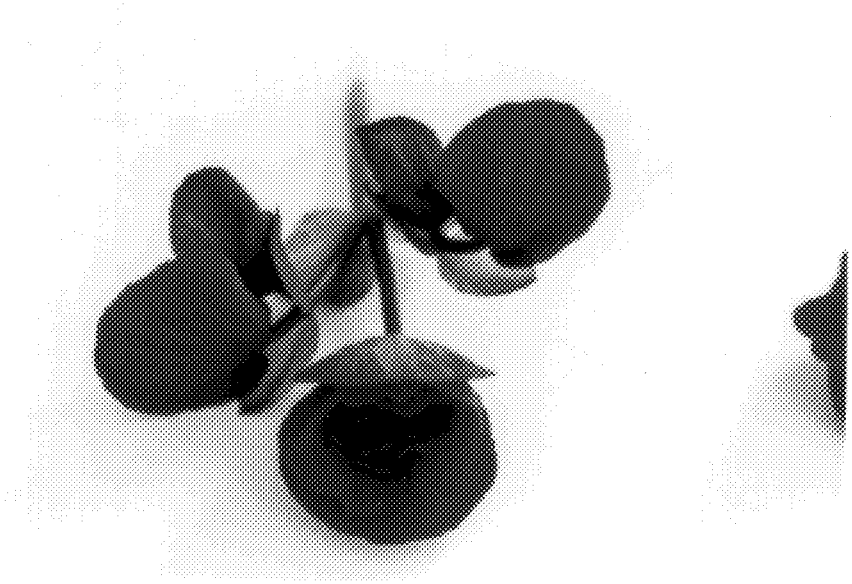

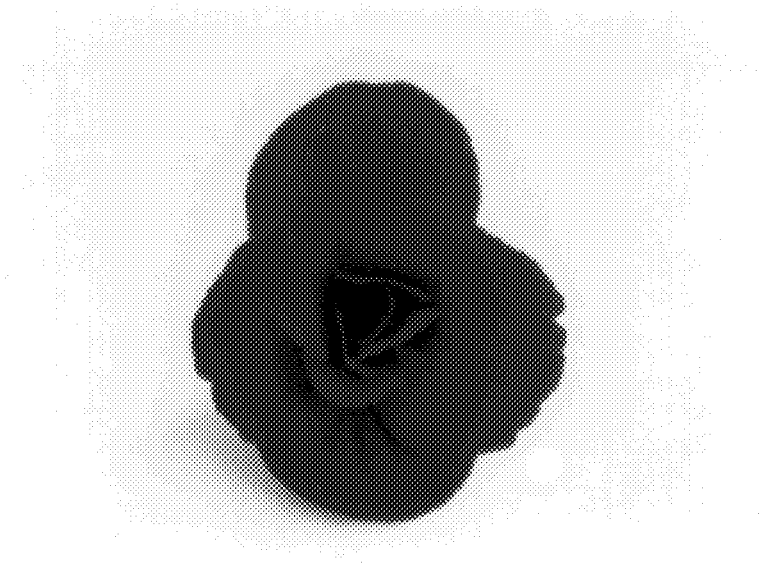

* * * * *